(12) United States Patent
Crum

(10) Patent No.: US 6,667,063 B2
(45) Date of Patent: Dec. 23, 2003

(54) NUTRITIONAL OR THERAPEUTIC SUPPLEMENT AND METHOD

(76) Inventor: Albert Crum, 77 Remsen St., Brooklyn Heights, NY (US) 11201

( * ) Notice: Subject to any disclaimer, the term of this patent is extended or adjusted under 35 U.S.C. 154(b) by 0 days.

(21) Appl. No.: 10/252,954

(22) Filed: Sep. 23, 2002

(65) Prior Publication Data

US 2003/0124198 A1 Jul. 3, 2003

Related U.S. Application Data

(63) Continuation-in-part of application No. 10/085,994, filed on Sep. 26, 2001, which is a continuation of application No. 09/371,812, filed on Aug. 11, 1999, now abandoned, which is a continuation-in-part of application No. 09/095,383, filed on Jun. 10, 1998, now abandoned.

(51) Int. Cl.[7] .......................... A61K 35/20; A61K 9/00; A01N 59/02; A23K 1/165
(52) U.S. Cl. ...................... 424/535; 424/702; 424/400; 424/442
(58) Field of Search ................................ 424/535, 702, 424/400, 442

(56) References Cited

U.S. PATENT DOCUMENTS

| | | |
|---|---|---|
| 4,377,569 A | 3/1983 | Plymate |
| 4,512,977 A | 4/1985 | Lundy |
| 4,784,852 A | 11/1988 | Johansson |
| 5,162,369 A * | 11/1992 | Ashmead et al. |
| 5,219,578 A | 6/1993 | Ansley |
| 5,451,412 A * | 9/1995 | Bounous et al. |
| 5,456,924 A | 10/1995 | Bounous et al. |
| 5,531,989 A | 7/1996 | Paul |
| 5,645,834 A | 7/1997 | Cockrum |
| 5,785,990 A | 7/1998 | Langrehr |
| 5,795,602 A | 8/1998 | Craig et al. |
| 5,846,569 A | 12/1998 | Anderson et al. |
| 5,889,038 A * | 3/1999 | Lencer et al. |
| 6,202,546 B1 * | 3/2001 | Scammell |

FOREIGN PATENT DOCUMENTS

| | | |
|---|---|---|
| EP | 0 184 267 A1 | 11/1986 |
| WO | WO 97/16977 | 5/1997 |

OTHER PUBLICATIONS

Badmaev, Vladimir et al. Alternative Therapies, vol. 2 No. 4: pp. 59–67 (1996).
Bounous, Gustavo et al. Clinical and Investigative Medicine vol. 12 No. 3 pp. 154–161 (1989).
Bounous, Gustavo et al., Journal of Nutrition vol. 113 No. 2: pp. 1415–1421 (1983).
Bounous, Gustavo et al. Journal of Nutrition vol. 115 No. 3: pp. 1403–1417 (1985).
Bounous, G. et al. Journal of Nutrition vol. 112: pp. 1747–1755 (1982.
Bounous, Gustavo et al., Journal of Infectious Diseases vol. 144 p. 281 (1981).
Bounous, Gustavo et al., Absorption & Utilization of Amino Acids vol. II: Chapter 14 pp. 219–133.
Kronhausen, Eberhard & Phyllis, Formula for Life, Chapter 9—pp. 45–52 (1989).
Kronhausen, Eberhard & Phyllis, Formula for Life, Chapter 10—pp. 53–54 (1989).

* cited by examiner

Primary Examiner—Christopher R. Tate
Assistant Examiner—Randall Winston
(74) Attorney, Agent, or Firm—Klauber & Jackson

(57) ABSTRACT

Nutritional compositions containing selenium, colostrum and whey are described. The compositions may be mixed with mammalian food to increase the concentration of glutathione in the mammalian body thereby to enhance the response of the mammal's immune system to infection.

15 Claims, No Drawings

NUTRITIONAL OR THERAPEUTIC SUPPLEMENT AND METHOD

CROSS-REFERENCE TO RELATED APPLICATIONS

This application is a continuation-in-part of copending and commonly owned application Ser. No. 10/085,994 filed Sep. 26, 2001 which is a continuation of application Ser. No. 09/371,812 filed Aug. 11, 1999, now abandoned, which application is a continuation-in-part of application Ser. No. 09/095,383 filed Jun. 10, 1998 now abandoned, all of which applications are herein specifically incorporated by reference in their entireties.

FIELD OF THE INVENTION

The present invention provides novel therapeutic nutritive compositions useful for increasing glutathione production in mammals, including humans, thereby to enhance the mammalian response to infection, stress or other trauma. More specifically, the invention provides novel food supplement compositions containing as the essential ingredients colostrum, a selected whey product and defined amounts of selenium or an organic or inorganic, water soluble selenium precursor.

BACKGROUND OF INVENTION

There are at the present time hundreds, perhaps thousands of food supplement compositions. Most of these compositions are designed to enhance the nutritional value of the food consumed by mammals including humans and animals, to increase energy levels, or to maintain electrolyte balance. These food supplements often comprise mixtures which if administered orally or parenterally are intended to bring to desired values the amount of vitamins, minerals, amino acids, salts and other materials required for proper nutrition in mammals. They are particularly valuable as sources of essential amino acids which may or may not be in foods but, in any event are destroyed or not synthesized by the metabolic processes of the mammalian body. Eight such amino acids are known. These include for example, leucine, isoleucine and phenylalanine.

The compositions may also contain small amounts of iron, zinc, calcium and other metals, non-metals and other ingredients thought to be necessary for proper nutrition. Some such supplements may contain as many as twenty different ingredients including natural and artificial flavoring agents, natural and artificial colors, binders, fillers and similar materials normally employed as excipients in such compositions.

Glutathione is a tripeptide and a major reducing agent in the mammalian body. Its chemical structure is:

or, more simply

Its chemical name is α-glutamyl-cysteinyl-glycine.

Like many other small peptides in the mammalian body, it is not synthesized by procedures involving DNA, RNA and ribosomes. Rather, it is synthesized from the amino acids available in the body by procedures utilizing enzymes and other body components such as adenosine triphosphate as an energy source.

Glutathione performs many functions in the mammalian body. One of its principal functions is as an antioxidant to reduce hydrogen peroxide and other oxidants thereby minimizing their deleterious effects. Another is to scavange free radicals. It has several other well substantiated detoxification activities.

The reduction of hydrogen peroxide is shown by the following simplified reaction sequence in which G represents glutathione, SH is the sulfhydryl group of the cysteine moiety and NAHD is an energy source:

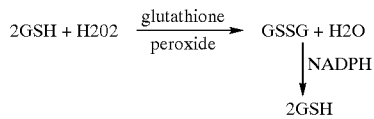

As will be seen, glutathione is regenerated after reducing hydrogen peroxide to water.

One of the most important contributions of glutathione to mammalian health is its participation in the proper functioning of the immune system to respond to infection or other types of trauma including, for example, chemotherapy, radiation therapy, stress and HIV infection. It is known that weakening of the immune system caused by these or other traumas occurs concurrently with depletion of glutathione in body tissues. It is known, also, that such weakening can be reversed by replenishing the supply of glutathione. It is believed that glutathione accomplishes its salutary effects by protecting immune cells against the ravages of oxidizing agents and free radicals.

There is some question as to whether orally ingested glutathione is available to enhance the immune system. Since it is a tripeptide, conventional wisdom suggests that it would be hydrolyzed in the intestinal system to release the free amino acids. Some experts are of the opinion that glutathione resists hydrolysis when taken orally. Even if some of this peptide gets through the gastrointestinal wall intact, it is questionable whether it can be absorbed as such into the individual cell rather than being synthesized intracellularly. In any event, it is generally acknowledged that an increase in tissue concentrations of glutathione facilitates resistance to invasion by infective agents by enhancing the immune system.

Whey is the curd-free portion of milk that remains after the production of cheese. "Whey" is a term referring to the serum or watery part of milk after removal of the cheese. Removal of a substantial portion of the water results in a dry whey. There are two types of dry whey. These are dry whey concentrates and dry whey isolates. The former (WPC) is an off-white to cream colored product which, depending on the method of manufacture, may contain from about 15% to 85% protein based on the total weight. It may additionally contain small amounts of minerals, vitamins and carbohydrates.

Whey protein isolate (WPI) contains more than 85% by weight of protein.

Both types of whey are available from Proliant, Manhattan, Ill.; Davisco Foods International, Inc. Eden Prairie, Minn. or Land-O-Lakes, Tulare, Calif.

A more important classification of whey for the understanding of this invention is that the whey is either denatured or undenatured.

Denatured whey which may be either WPC or WPI is whey in which the globular structure of the constituent protein has been disrupted into a random coil formation or has been partially hydrolyzed. Such disruption may be caused by heat, pumping, mixing, aeration, vacuum evaporation, drying or other processing operations. Undenatured whey is prepared under carefully controlled conditions so that the protein structure is substantially the same as in the milk from which it was obtained.

Whey products exist commercially or are otherwise known which are substantially undenatured or in which the whey has undergone various degrees of denaturization. The immune regulating or chemical activities of these products generally vary with the degree of denaturation.

Sometimes a specific activity is eliminated by any degree of denaturation. For example, as will be explained in more detail below, undenatured and denatured WPC or WPI have substantially the same nutritional value in mammals, but denaturization abolishes the ability of the products to modulate immunological activity.

The cost of undenatured whey tends to decrease directly with the degree of denaturation. Whey products in which the degree of denaturation is less than 10–15 percent are too expensive for use in products intended for general use by humans or in animal feeds. Although undenatured whey is known to enhance immunological activity, the art has long been seeking whey products and compositions which retain immunological modulating activity without being prohibitively expensive.

Colostrum is a thin milky fluid secreted by the mammary gland of mammals a few days before or after parturition. It is a unique combination of beneficial nutrients including protective antibodies, fat, carbohydrate, vitamins and minerals.

The immunological components of colostrum include IgG, IgM and IgA. These components confer passive immunity to the neonate and protection against infection during the initial period after parturition. After this period, colostrum is no longer absorbed through the gut and the newborn must depend upon its own developing immune system for protection.

Colostrum is an important factor in the growth of mammals including humans, bovines, caprines, porcines and equines. The preferred colostrums for use in the compositions of this invention are bovine and caprine. Several colostrum products useful in the practice of this invention are commercially available.

The compositions of this invention are often employed together with soluble dietary fibers such as inulin and fructo-oligosaccharides (FOS), although the use of these materials is optional. They may be mixed into the same dosage unit as the novel compositions of the invention or separately administered, usually concurrently. When inulin or FOS are utilized, the beneficial bifidobacteria increase significantly in the intestine and the concentration of pathogenic microorganisms decreases.

Both inulin and FOS are commercially available. Inulin is a fructose polysaccharide available from many sources including onion, asparagus, artichoke and cereal grains. FOS are widely distributed in nature and can be readily extracted from bananas, tomatoes, garlic, onions, artichoke, barley and soybeans.

SUMMARY OF THE INVENTION

This invention provides compositions and methods for enhancing the mammalian immune system thus affording improved resistance against infections, chronic stress or other traumas. These results are believed to be attained by increasing the glututhione concentration in body tissues.

The compositions of this invention contain as essential ingredients selected catalytic quantities of elemental selenium or a non-toxic water soluble, organic or inorganic salt, chelate or other selenium compound as a precursor of elemental selenium; a specifically selected whey product and a mammalian colostrum.

The novel compositions may be prepared by conventional methods well known to the skilled artisan and may be provided in a wide variety of forms suitable for the selected method of administration. They may be provided in dosage unit form or in bulk form.

The compositions may be delivered in or with a human food including, for example, milk, milk shakes, ice cream, fruit juice, soy milk and yogurt or as powders to be sprinkled on meats, salads or other foods. They may be incorporated into solid foods such as candy bars, cereals, health bars and other comestibles. They may be delivered as a constituent of animal feeds as a powder or other convenient form. They may also be delivered with any of a number of medicinals such as antimicrobial agents including antibiotics and antiviral agents.

The compositions may be used when mixed with other ingredients such as inulin, FOS, probiotics such as *Lactobacillus rhammus* HN001, Lactobacillus GG or others of the Lactobacilus or *Bifidobacteria genera*; vitamins, minerals, and additional conventional additives often employed in nutritional supplements.

Customary excipients such as water, oils, flavoring agents, preservatives, alcohol, coloring agents and the like may be used in the formulations.

DETAILED DESCRIPTION OF THE INVENTION

The essential components in the compositions of this invention are a selected whey product, colostrum and a non-toxic catalytic quantity of elemental selenium or a water soluble precursor of elemental selenium in an amount sufficient to aid in the production of glutathione. Selenium precursors are much preferred since they are easier to handle.

Selenium is one of numerous trace metals found in many foods. In the compositions of this invention, selenium may be employed as one of several non-toxic, water soluble, organic or inorganic selenium compounds capable of being absorbed by the body. The presently preferred inorganic selenium compounds are aliphatic metal salts containing selenium in the form of selenite or selenate anions. However, organic selenium compounds are more preferred because they are normally less toxic than inorganic compounds. Other selenium compounds which may be mentioned by way of examples include selenium cystine, selenium methionine mono- and di-seleno carboxylic acids with about seven to eleven carbon atoms in the chain. Seleno amino acid chelates are also useful.

As will be explained more fully below, selenium compounds are utilized in the novel compositions in amounts to provide selected quantities of elemental selenium.

It is important for the practice of this invention that the selenium in the form present in the composition be capable of being absorbed by the body tissue of the patient under treatment. It is noted that water insoluble selenium compounds are not generally absorbed.

For convenience, the term "selenium" is sometimes used hereinafter to include any of the various water soluble selenium products which can be employed in the practice of this invention. It will be understood, however, that the particular forms of selenium compounds set forth herein are not to be considered limitative. Other selenium compounds which exhibit the desired activity, are non-toxic and are compatible with other components in the mixture can be employed. Many of them are available commercially.

The whey product may be up to about 35% denatured. The whey product may be completely denatured, but as mentioned above the cost of wholly denatured whey is such that it is not feasible to employ wholly undenatured whey in compositions to serve general human consumption or in animal needs.

Wholly undenatured whey can be prepared as described by Bounous et al in U.S. Pat. No. 5,290,571 which describes a number of biological activities for the wholly undenatured product including enhanced immunological effects which are associated with increased production of glutathione. This same patent at column 28, lines 16 through 24 teaches that the immunoenhancing activity of undenatured whey protein is dependent upon its undenatured (native) state.

Another patent (U.S. Pat. No. 5,451,412) by the same inventive entity, at column 10, lines 30 to 33, specifically state that denaturation abolishes the described biological activity without affecting the nutritional quality of the whey protein concentrate. The whey protein concentrate referred to in this teaching is the same whey product described in the '571 patent.

Unexpectedly, it has now been discovered that when employed as a component in the tripartite compositions taught herein, it is not necessary to employ wholly undenatured native whey. In fact, the dry whey product used in the novel compositions of the invention may contain up to about 35% denatured whey without serious impairment of immunoenhancing activity. Whatever loss of activity results with some denaturation is not sufficient to require the use of undenatured whey and the resulting expense. Thus, the compositions of this invention can be employed in nutritional products available at reasonable cost to the general public and to those engaged in animal husbandry.

Of course, the invention also embraces compositions in which the whey component is highly undenatured, even up to about 100% undenatured. Such compositions would be useful with patients having an acute need of enhanced immunological activity without regard to cost. This would include, for example, patients with an advanced AIDS infection or sepsis. Veterinarian use might be justified with prize animals such as valuable racing horses.

Accordingly, the dried whey product utilized in the novel compositions will be a WPC or WPI which is up to about 35% denatured or, conversely about 65% to about 100% undenatured. Preferably, it will contain from about 65% to about 85% protein. It may comprise from about 5% to about 95% of the composition based on the total weight of the composition.

Several whey products are available commercially and may be employed in the practice of this invention.

One such product Proliant™ 8010 Instantized is available from Proliant with headquarters in Manhattan, Ill. It is a WPC. Its typical properties are reported as:

| PROLIANT ™ 8010 NUTRITIONAL PROFILE (per 100 g of product) | |
| --- | --- |
| Protein-dry basis (g) | 81.2 |
| Protein-as is (g) | 76.0 |
| Moisture (g) | 6.4 |
| Ash (g) | 2.7 |
| Carbohydrates (g)-calculated | 10.2 |
| Lactose (g) | 4.4 |
| Fat (g) | 4.7 |
| Cholesterol (mg) | 184 |
| *Total Calories (Kcal) | 387 |

| -continued | |
| --- | --- |
| MINERALS (per 100 g product) | |
| Calcium (mg) | 560 |
| Phosphorus (mg) | 376 |
| Sodium (mg) | 187 |
| Potassium (mg) | 456 |
| Magnesium (mg) | 59 |
| Chloride (mg) | 83 |
| VITAMINS (per 100 g product) | |
| Vitamin A (IU) | 194 |
| B-Carotene (IU) | 51 |
| Retinol (IU) | 143 |
| Vitamin C (mg) | <1.0 |
| Vitamin B1 (mg) | 0.5 |
| Vitamin B2 (mg) | 0.7 |
| Vitamin B12 (mcg) | 6.6 |
| PROLIANT™ 8010 AMINO ACID PROFILE (G/100 g protein-as is) | |
| Alanine | 5.6 |
| Arginine | 2.6 |
| Aspartic Acid | 10.5 |
| Cystine/Cysteine | 2.5 |
| Glutamic Acid | 15.3 |
| Glycine | 1.9 |
| Histidine | 2.3 |
| Isoleucine | 4.9 |
| Leucine | 10.7 |
| Lysine | 10.1 |
| Methionine | 2.0 |
| Phenylalanine | 3.7 |
| Proline | 5.4 |
| Serine | 5.1 |
| Threonine | 6.3 |
| Tryptophan | 1.8 |
| Tyrosine | 3.4 |
| Valine | 6.0 |

*Analysis is done by calculation

WPC is also commercially available in a heat stable form from the same company as Proliant™8200. Its typical properties are reported as:

| PROLIANT ™ 8200 NUTRITIONAL PROFILE (per 100 g) of product) | |
| --- | --- |
| Protein-dry basis (g) | 81.8 |
| Protein-as is (g) | 78.3 |
| Moisture (g) | 4.3 |
| Ash (g) | 4.4 |
| Carbohydrates (g)-calculated | 8.5 |
| Lactose (g) | 3.8 |
| Fat (g) | 4.5 |
| Cholesterol (mg) | 177 |
| *Calories (Kcal) | 388 |
| MINERALS (per 100 g product) | |
| Calcium (mg) | 301 |
| Phosphorus (mg) | 510 |
| Sodium (mg) | 973 |
| Potassium (mg) | 556 |
| Magnesium (mg) | 41 |
| Chloride (mg) | 445 |

-continued

VITAMINS (per 100 g product)

| | |
|---|---|
| Vitamin A (IU) | 136 |
| B-Carotene (IU) | 26 |
| Retinol (IU) | 110 |
| Vitamin C (mg) | <1.0 |
| Vitamin B1 (mg) | 0.1 |
| Vitamin B2 (mg) | 0.9 |
| Vitamin B12 (Mcg) | 8.5 |

PROLIANT™ 8200 AMINO ACID PROFILE
(G/100 g protein-as is)

| | |
|---|---|
| Alanine | 5.1 |
| Arginine | 2.3 |
| Aspartic Acid | 10.5 |
| Cystine/Cysteine | 2.3 |
| Glutamic Acid | 16.9 |
| Glycine | 1.6 |
| Histidine | 1.6 |
| Isolucine | 5.9 |
| Leucine | 10.4 |
| Lysine | 10.3 |
| Methionine | 2.0 |
| Phenylalanine | 3.0 |
| Proline | 6.0 |
| Serine | 5.1 |
| Threonine | 6.5 |
| Tryptophan | 1.6 |
| Tyrosine | 3.4 |
| Valine | 5.5 |
| Hydroxyproline | <0.01 |

*Analysis is done by calculation

It will be noted that the principal difference between the two products is the variation in mineral content.

For applications of this invention in which the product is to be heated, the preferred whey is heat stable. This form of WPC is preferred if the novel compositions are to be employed in foods, the preparation of which requires heat, for example a pasteurized beverage.

Heat stable whey is also available from Davisco and Land-O-Lakes.

Selenium catalyzes the production of glutathione. The compositions of this invention contain catalytic quantities of elemental selenium or a non-toxic water soluble, organic or inorganic salt, chelate or other selenium compound as a precursor of elemental selenium.

The recommended daily allowances for elemental selenium as reported in the Pharmacological Basis of Therapeutics, Ninth Edition, page 1540, The McGraw-Hill Companies, 1996 are as follows:

| | Years | μg |
|---|---|---|
| Infants | 0.0–0.5 | 10 |
| | 0.5–1.0 | 15 |
| Children | 1–3 | 20 |
| | 4–6 | 20 |
| | 7–10 | 30 |
| Males | 11–14 | 40 |
| | 15–18 | 50 |
| | 19–24 | 70 |
| | 25–50 | 70 |
| | 51+ | 70 |
| Females | 11–14 | 45 |
| | 15–18 | 50 |
| | 19–24 | 55 |
| | 25–50 | 55 |

-continued

| | Years | μg |
|---|---|---|
| | 50+ | 55 |
| Pregnant | — | 65 |
| Lactating | 1st six months | 75 |
| | 2nd six months | 75 |

The recommended daily dosage for humans, therefore ranges from 10 to 75 μg per day. For animals the range may be generally higher but will, of course depend upon the animal and its size.

The catalytic quantity of selenium or selenium precursor utilized in the compositions of this invention is such that the compositions will contain in one dosage unit or in multiple dosage units sufficient elemental selenium to promote the production and activation of glutathione. Typically, this will be at or near the recommended daily allowance of selenium for the individual mammal under treatment. This amount will be below the toxicity limit for elemental selenium.

The other essential ingredient in the nutritive compositions of the present invention is colostrum—the "premilk" of lactating mammals. Spray dried bovine and caprine colostrums are the presently preferred colostrums. They are both commercially available.

The amount of colostrum utilized to achieve the benefits of the invention may vary over a wide range, i.e. from about 5% to about 95% based on the total weight of the three essential components of the compositions.

The presently preferred ratios of whey product to colostrum in the novel compositions is from about 2:1 to about 1:1 since this range provides the optimum balance of price and activity.

The daily effective dosage of the products of this invention will depend upon the size of the individual (human or animal) being treated, the condition being treated, the age of the individual and other factors well known to the physician or veterinarian in attendance. The optimum daily dosage can easily be determined by a few simple observations. It will generally vary from about 10 g to 250 g per day for humans and small animals. For large animals the daily dosage will normally be from about 100 g to 1000 g per day.

As the term is used herein, "effective dosage" means that dosage which will bring about the desired result, i.e. enhancement of the immune system.

The selected dosage per day may be administered in one dose or in intermittent dosages throughout the day. The compositions may be provided for humans or animals in powdered form to be mixed with any of a variety of raw, processed, cooked or uncooked foods. A preferred method of administration with animals is as a powder mixed with the animals feed. For humans a preferred dosage unit is a tablet, capsule or other orally ingested form containing the selected amount of the composition.

A dosage unit may be administered separately or together with other nutritional products such as vitamins and minerals. If the compositions are employed together with other ingredients, the separate components need not be provided in one dosage form. They may be individually added to produce the total mixture, but in the amounts described above.

The novel preparations of the invention may be made by any of a number of conventional methods. Typically, the components will be combined in one preparation as the active ingredient in intimate admixture with a suitable carrier according to usual compounding techniques. Dosage units may take a wide variety of forms depending upon the intended method of administration, e.g., oral, sublingual, buccal, nasal, anal or parenteral.

In preparing the compositions in oral dosage form, any of the usual pharmaceutical carriers may be employed. For oral liquid preparations (e.g., suspensions, elixirs, and solutions), carriers containing water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, gelatin capsules, pills, and tablets). Lozenges, chewable tablets and controlled release forms may also be used. If desired, tablets may be sugar coated or enteric coated by standard techniques. Examples of additional inactive components which provide for easier oral administration include but are not limited to beeswax, lecithin, gelatin, purified water, and glycerin.

As stated above, oral dosage formulations of the compositions may be added to foods and consumed. Any conventional foodstuff may be appropriate as a carrier for the presently disclosed compositions. The compositions may be added to the carrier as one composition or as separate ingredients. If the whey, colostrum and selenium or selenium precursor are added separately, the amounts of each ingredient should be in the ratios defined herein. The components may be provided in containers to be combined by the user.

For parenteral products, the carrier will usually comprise sterile water, although other ingredients may be included, e.g., to aid solubility or for preservation purposes. Injectable suspensions may also be prepared, in which case appropriate liquid carriers, suspending agents, adjuvants, and the like may be employed.

As will be clear from the foregoing, the nutritive supplement compositions of the present invention may optionally contain other ingredients that aid in processing or storage of the compositions or that improve their nutritional or therapeutic properties. Such optional ingredients include maltodextrin, dextrose, fructose, canola oil, corn syrup solids, natural or artificial flavors or colors, guar gum, refined cellulose, rice paste, dicalcium phosphate, sodium caseinate, medium chain triglycerides, dipotassium phosphate, magnesium oxide, lecithin, ascorbic acid, inositol, choline bitartrate, vitamin E acetate, nicotinamide, calcium pantothenate, ferrous fumarate, zinc sulfate, pyridoxine hydrochloride, riboflavin, thiamine mononitrate, manganese sulfate, vitamin A palmitate, copper gluconate, folic acid, folate, biotin, sodium molybdate, potassium iodide, chromium picolinate, various vitamins, para aminobenzoic acid, glutamine, and beta-carrrotene. Additional ingredients known in the art to function as dietary supplements such as herbal compounds are intended to be within the scope of the present invention. These optional ingredients are particularly applicable to oral dosage forms. Dosage forms and bulk forms containing vitamins, minerals and other nutritional components are prepared from the various combinations which can be derived from the following list:

| Ingredient | Amount |
| --- | --- |
| whey protein | 0.01 g–100 g |
| FOS | 0.01 g–50 g |
| bovine or caprine colostrum | 0.01 g–100 g |
| maltodextrin | 1 g–30 g |

-continued

| Ingredient | Amount |
| --- | --- |
| dextrose | 1 g–30 g |
| fructose | 1 g–30 g |
| canola oil | 0.1 g–0.5 g |
| corn syrup solids | 1 g–50 g |
| natural flavors | 0.001 μg–1 mg |
| artifical flavors | 0.0001 μg–1 mg |
| natural colors | 0.0001 μg–10 mg |
| artifical colors | 0.0001 μg–5 mg |
| guar gum | 0.001 g–10 g |
| refined cellulose | 0.01 g–10 g |
| dicalcium phosphate | 0.5 g–3 g |
| sodium caseinate | 0.01 g–5 g |
| medium chain triglycerides | 0.1 g–0.6 g |
| dipotassium phosphate | 0.1 g–5 g |
| magnesium oxide | 0.01 g–0.9 g |
| lecithin | 0.015 g–0.6 g |
| ascorbic acid | 0.02 g–0.3 g |
| inositol | 0.01 g–1 g |
| choline bitartrate | 0.01 g–1 g |
| vitamin E acetate | 10 IU–200 IU |
| nicotinamide | 0.0005 g–0.05 g |
| calcium pantothenate | 0.01 g–0.5 g |
| ferrous fumarate | 0.002 g–0.3 g |
| zinc sulfate | 0.005 g–0.06 g |
| pyridoxine hydrochloride | 0.001 g–0.25 g |
| riboflavin | 0.0005 g–0.1 g |
| thiamine mononitrate | 0.0005 g–0.1 g |
| manganese sulfate | 0.0005 g–0.1 g |
| vitamin A palmitate | 2,500 IU–5,000 IU |
| copper gluconate | 0.0005 g–0.006 g |
| folic acid | 400 μg–2.5 mg |
| folate glutamate | 400 μg–0.002 g |
| biotin | 100 μg–600 μg |
| sodium molybdate | 15 μg–500 μg |
| potassium iodide | 50 μg–500 μg |
| chromium picolinate | 25 μg–500 μg |
| phytonadione | 10 μg–500 μg |
| vitamin D3 | 200 IU–800 IU |
| PABA | 1 μg–1000 μg |
| cyanocobalamin | 0.1 μg–1000 μg |
| glutamine | 0.2 g–4 g |
| beta-carotene | 5,000 IU–25,000 IU |

Selenium is preferably added in any of its precursor forms to the above ingredients in amounts of from about 5 μg to 200 μg.

Nutritional wafers are within the scope of the invention. Typical wafers may weigh for example about 20 grams. A typical composition of the wafer would include about 16.6 grams of Proliant whey, about 1000 mg of colostrum and about 7 μg of selenium. The remaining constituents of the wafer would include appropriate fillers, extenders, sweeteners and natural flavorings in various combinations, such as refined cellulose, maltodextrin, fructose, rice paste or other fillers, extenders, sweeteners and natural flavorings known to the skilled artisan.

A particular advantage of the compositions of the invention is that they can be provided in a number of different forms and at dosage levels appropriate to the individual mammal being treated. For example, tablets, elixirs, solutions, emulsions, powders, capsules and other forms can be provided for one a day treatment or successive treatments on the same day for animals or humans whether male or female, whether infant, adolescent or adult. The defining feature of this advantage is the amount of selenium precursor utilized since the other components are essentially non-toxic.

Referring to the table above, tablets and other forms of the immunoenhancing compositions can be prepared to provide any quantity of elemental selenium from less than 10 μg to 75 μg. For example, a tablet containing 100 μg of selenium methionine is capable of delivering 40 μg of elemental selenium, and 75 μg of selenium methionine is capable of delivering 30 μg of selenium.

Examples of these suitable carriers for use in this invention are described in Remington's Pharmaceutical Sciences, Eighteenth Edition (1990), Mack Publishing Company, Easton, Pa., in Handbook of Pharmaceutical Excipients, published by The American Pharmaceutical Association and The Pharmaceutical Society of Great Britain (1986) and the Handbook of Water-Soluble Gums and Resins, ed. By R. L. Davidson, McGraw-Hill Book Co., New York, N.Y. (1980). These publications are incorporated by reference herein in their entirety. They can be readily employed by the skilled artisan to devise methods of delivery and dosage forms other than those specifically described in this disclosure.

The following examples are given by way of illustration only. They are not to be considered as limitations of the invention since many apparent variations are possible without departing from its spirit or scope.

EXAMPLE 1 (TABLET)

| Ingredients: | |
|---|---|
| Whey (Proliant ™ 8010 or 8200) | 1 gm |
| Colostrum | 1 gm |
| Selenium methionine | 5 μg |

Blend the ingredients together and pass through a 60 mesh screen and tumble until the components are thoroughly mixed. Compress using a 7/16 inch standard concave punch.

EXAMPLE 2 (POWDER)

| Ingredients: | |
|---|---|
| Whey (Proliant ™ 8010 or 8200) | 75 gm |
| Colostrum | 25 mg |
| Selenium methionine | 15 μg |

Thoroughly mix the ingredients in a blender and pass through a 80 mesh screen.

This powder may be used for mixing with animal feeds, frostings, fruit spreads and beverages to be pasteurized.

EXAMPLE 3 (CHEWABLE TABLET)

| Ingredients: | | |
|---|---|---|
| Vitamin A USP (dry, stabilized form) | 500 | USP units |
| Vitamin D USP (dry, stabilized form) | 400 | USP units |
| Ascorbic Acid USP | 60.0 | mg |
| Thiamine Hydrochloride USP | 1 | mg |
| Riboflavin USP | 1.5 | mg |
| Pyridoxine Hydrochloride USP | 1 | mg |
| Cyanocobalamin USP | 2 | μg |
| Calcium Pantothenate USP | 3 | mg |
| Niacinamide USP | 10 | mg |
| Mannitol USP (granular) | 236.2 | mg |
| Corn Starch | 16.6 | mg |
| Sodium saccharin | 1.1 | mg |
| Magnesium stearate | 6.6 | mg |
| Talc USP | 10 | mg |
| Whey (Proliant ™ 8010) | 8 | g |

| -continued | |
|---|---|
| Ingredients: | |
| Colostrum | 500 mg |
| Selenium methionine | 7 μg |

Thoroughly mix the ingredients in a blender and compress using a 3/8 inch bevel-edge punch.

What is claimed is:

1. A non-toxic nutritional composition useful to increase glutathione production in a mammal thereby to enhance the immune activity of the mammal, said composition containing as essential active ingredients:
    a: a catalytic quantity of elemental selenium or a water soluble selenium precursor;
    b: from about 5% to about 95% of a whey product selected from the group consisting of whey protein concentrates and whey protein isolates containing from about 65% to about 85% protein which is from about 65% to about 100% undenatured; and
    c: from about 5% to about 95% by weight of colostrum; the percent by weight of each component based on the total weight of the composition.

2. The composition of claim 1, wherein the whey product is heat stable.

3. The composition of claim 1, wherein the colostrum is caprine colostrum.

4. The composition of claim 1, wherein the colostrum is bovine colostrum.

5. The composition of claim 1 in bulk form.

6. The composition of claim 1 in dosage unit form.

7. The composition of claim 6, wherein the dosage unit is in powder, tablet or capsule form.

8. The composition of claim 1, 2, 3, 4, 5, 6 or 7, wherein the ratio of whey to colostrum is about 2:1 to 1:1.

9. The composition of claim 1 as a component in a milk shake.

10. The composition of claim 1 as a component in yogurt.

11. The composition of claim 1 as a component in a health bar.

12. A method of treating a mammal to increased glutathione production in the mammal thereby to enhance the immune activity of the mammal which comprises administering to the mammal an immune response enhancing amount of a composition containing as essential active ingredients:
    a) a catalytic quantity of elemental selenium or a water soluble selenium precursor;
    b) from about 5% to about 95% of a whey product selected from the group consisting of whey protein concentrates and whey protein isolates containing front about 65% to about 85% protein which is from about 65% to about 100% undenatured;
    c) from about 5% to about 95% by weight of colostrum; the percent by weight of each component based on the total weight of the composition.

13. A method as in claim 12, wherein the whey product is heat stable.

14. The method as in claim 12, wherein the mammal is an animal and the composition is administered as an ingredient in the animals feed.

15. The method as in claim 12, wherein the mammal is human and the composition is administered as a nutritional supplement in a food.

* * * * *